(12) United States Patent
Ilsemann et al.

(10) Patent No.: US 9,402,801 B2
(45) Date of Patent: Aug. 2, 2016

(54) ACTIVE INGREDIENT COMBINATIONS OF MAGNOLIA BARK EXTRACT AND HYALURONIC ACID AND THE COSMETIC AND/OR DERMATOLOGICAL USE THEREOF

(71) Applicant: Beiersdorf AG, Hamburg (DE)

(72) Inventors: Corinna Ilsemann, Hamburg (DE); Marc Winnefeld, Wedel (DE); Torsten Schlaeger, Hamburg (DE); Ursula Holtzmann, Hamburg (DE); Sarah Hiddemann, Hamburg (DE); Nadeshda Kurz, Hamburg (DE); Joanna Ruhs, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 14/411,688

(22) PCT Filed: Jun. 13, 2013

(86) PCT No.: PCT/EP2013/062274
§ 371 (c)(1),
(2) Date: Dec. 29, 2014

(87) PCT Pub. No.: WO2014/005818
PCT Pub. Date: Jan. 9, 2014

(65) Prior Publication Data
US 2015/0164780 A1   Jun. 18, 2015

(30) Foreign Application Priority Data

Jul. 6, 2012 (DE) .......................... 10 2012 211 807

(51) Int. Cl.
| | | |
|---|---|---|
| A61K 36/00 | (2006.01) | |
| A61K 8/97 | (2006.01) | |
| A61K 8/73 | (2006.01) | |
| A61Q 19/06 | (2006.01) | |
| A61Q 19/08 | (2006.01) | |
| A61K 31/728 | (2006.01) | |
| A61K 36/575 | (2006.01) | |

(52) U.S. Cl.
CPC ... *A61K 8/97* (2013.01); *A61K 8/73* (2013.01); *A61K 8/735* (2013.01); *A61K 31/728* (2013.01); *A61K 36/575* (2013.01); *A61Q 19/06* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 7,744,932 | B2 | 6/2010 | Faller et al. |
| 8,084,066 | B2 | 12/2011 | Faller et al. |
| 8,445,036 | B2 | 5/2013 | Faller et al. |
| 8,758,839 | B2 | 6/2014 | Faller et al. |
| 2008/0260869 | A1 | 10/2008 | Faller et al. |
| 2010/0143515 | A1 | 6/2010 | Faller et al. |
| 2011/0033562 | A1 | 2/2011 | Faller et al. |
| 2012/0058209 | A1 | 3/2012 | Faller et al. |
| 2012/0093953 | A1 | 4/2012 | Faller et al. |

FOREIGN PATENT DOCUMENTS

| | | | | |
|---|---|---|---|---|
| DE | WO 2006128584 A1 * | 12/2006 | ............ | A61K 8/731 |
| DE | 102008034265 A1 | 1/2010 | | |
| DE | 102010015788 A1 * | 10/2011 | | |
| DE | 102010015789 A1 | 10/2011 | | |
| DE | 102010015790 A1 * | 10/2011 | ............ | A61K 8/347 |
| DE | 102010063895 A1 | 6/2012 | | |
| WO | 02102347 A1 | 12/2002 | | |
| WO | 2007107856 A1 | 9/2007 | | |
| WO | WO 2009082511 A1 * | 7/2009 | | |

OTHER PUBLICATIONS

Farwick et al, Low molecular weight hyaluronic acid: its effects on epidermal gene expression & skin ageing. SOFW Journal (2008), 134(11), 17-18, 20, 22.*
"Korres Magnolia Bark Day Cream for First Wrinkles, Tagescreme mit Magnolienrindenextrakt für erste Fältchen 40ml", Apr. 27, 2012, pp. 1-2, Found on Internet: URL:https://web.archive.org/web/2012042723 5134/http://www.greenglam . . . 1 of [found on Jan. 22, 2014].
Anonymous: "DaUnBee Activating Liposome Lotion(120ml) from SkinCure, Inc., Korea", Sep. 28, 2009, Found on Internet: URL:http://www.ec21.com/product-details/DaUnBee-Activating-Liposome-Lotion-120ml--6395960.html [found on Jan. 23, 2014].

* cited by examiner

*Primary Examiner* — Qiuwen Mi
(74) *Attorney, Agent, or Firm* — Abel Law Group, LLP

(57) ABSTRACT

The invention relates to active ingredient combinations of *magnolia* bark extract and hyaluronic acid, cosmetic and/or dermatological preparations containing said active ingredient combinations and to the use thereof for the cosmetic and/or dermatological treatment and/or prophylaxis of cellulite and/or the appearance form of skin aging.

20 Claims, 1 Drawing Sheet

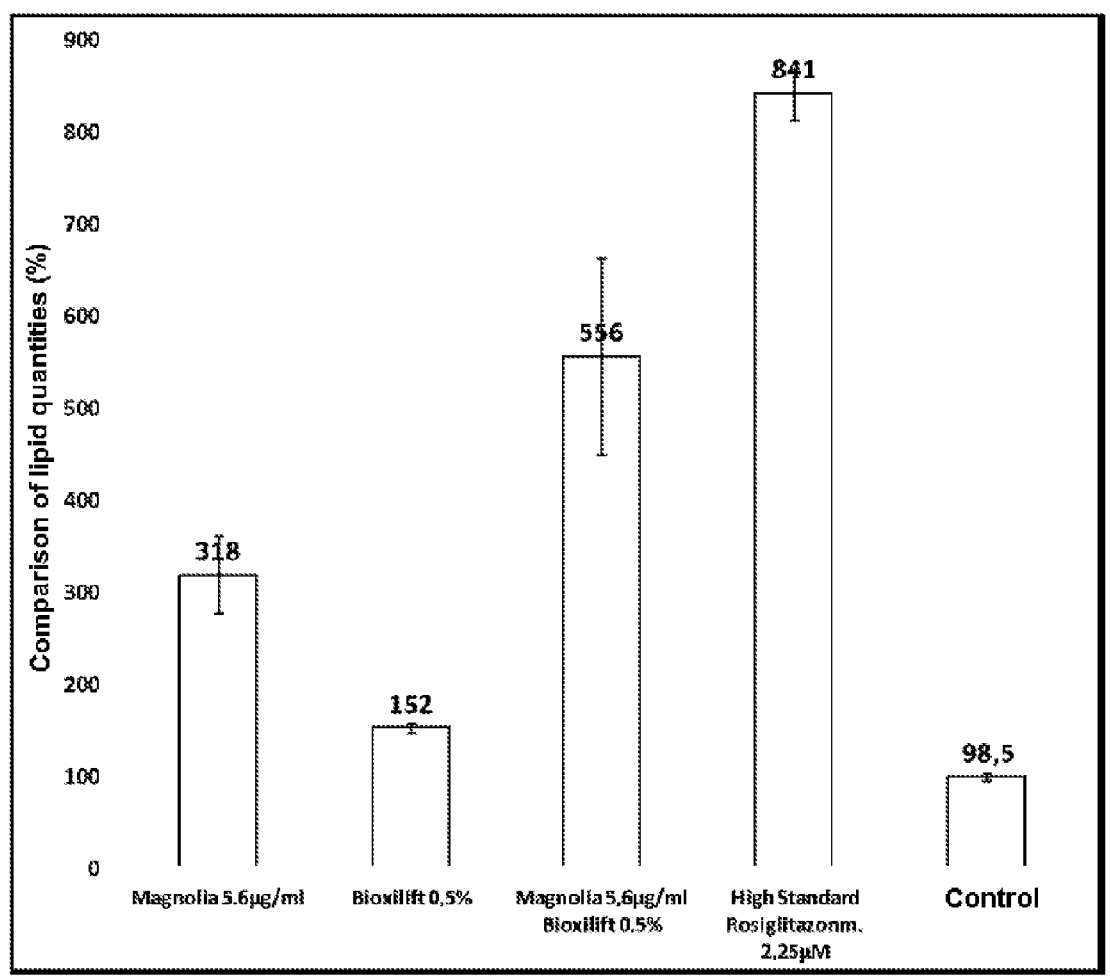

ACTIVE INGREDIENT COMBINATIONS OF MAGNOLIA BARK EXTRACT AND HYALURONIC ACID AND THE COSMETIC AND/OR DERMATOLOGICAL USE THEREOF

BACKGROUND OF THE INVENTION

1. Field of the Invention

The present invention relates to cosmetic and/or dermatological preparations comprising active ingredients for the care and protection of the skin, in particular sensitive skin, such as also very particularly at the forefront skin aged or aging as a result of intrinsic and/or extrinsic factors, and also the use of such active ingredients and combinations of such active ingredients in the fields of cosmetic and dermatological skin care.

2. Discussion of Background Information

The term "cosmetics" can be used to encompass all measures which, for esthetic reasons, bring about changes to skin and hair or are used for cleaning the body. "Cosmetics" thus means to care for, improve and to beautify the external appearance of the body in order, in a way which can be seen, felt or smelled, to provide pleasure both to those around us and to ourselves.

Impairment of this function may lead to increased absorption of toxic or allergenic substances or to attack by microorganisms and consequently to toxic or allergic skin reactions.

It is also an aim of skin care to compensate for the loss of sebum and water by the skin caused by daily washing. This is particularly important if the natural regeneration ability is inadequate. Moreover, skin care products are intended to protect against environmental influences, in particular against sun and wind, and delay skin aging.

Chronological skin aging is caused e.g. by endogenous, genetically determined factors. The following structural damage and functional disorders, also covered by the term "senile xerosis", for example, occur in the epidermis and dermis as a function of aging:
a) dryness, roughness and formation of dryness wrinkles,
b) itching and
c) reduced refatting by sebaceous glands (e.g. after washing).

Exogenous factors, such as UV light and chemical noxae, can have a cumulative effect and increase the rate of and/or supplement e.g. the endogenous aging processes. In the epidermis and dermis, for example, the following structural damage and functional disorders arise in the skin in particular as a result of exogenous factors, over and above the degree and grade of the damage in the case of chronological aging:
d) visible vascular dilations (telangiectases, couperosis);
e) sagging, volume loss and formation of wrinkles;
f) local hyper-, hypo- and mal-pigmentations (e.g. age spots) and
g) increased susceptibility to mechanical stress (e.g. cracking).

The present invention relates in particular to products for the care of skin aged in a natural way, and to the phenomena listed under a), e) and g).

Products for caring for sagging, in particular aged skin are known per se. They comprise e.g. retinoids (vitamin A acid and/or derivatives thereof) and vitamin A and/or derivatives thereof. However, their effect is limited in terms of extent to structural damage. Moreover, there are considerable difficulties during product development in stabilizing the active ingredients to an adequate extent against oxidative degradation. The use of vitamin A acid-containing products, moreover, often brings about highly erythematous skin irritations. Retinoids can therefore only be used in low concentrations.

Sagging skin is often linked with an accompanying phenomenon of obesity and/or cellulite, which is often associated therewith.

The body awareness of consumers has increased significantly in recent years. In this connection, as well as cleaning and care applications, measures are also increasingly being taken to improve the silhouette of the body. Cellulite—a widespread phenomenon—assumes a central position in this connection. The visible appearance of cellulite is based on an increase in fat pads in the subcutis (subcutaneous fatty tissue), a weakening of the connective tissue and also a reduction in the flow ratios in the blood stream and lymphatic tracts. The cause is therefore in part a position-dependent weakening of the connective tissue with the simultaneous appearance of enlarged fatty cell chambers as a result of excess weight, an unbalanced diet and lack of exercise. The formation of cellulite can also be attributed to increased permeability of the capillary walls, which allows water to penetrate into the connective tissue.

In addition, there may be a localized testosterone deficiency at the areas of skin affected. In any case, cellulite is a phenomenon which is almost never observed in men.

SUMMARY OF THE INVENTION

The object of the present invention was therefore to find ways which avoid the disadvantages of the prior art. In particular, it was an object of the present invention to provide preparations which can effect advantageous tightening of sagging skin.

Surprisingly, it has been found that active ingredient combinations of *magnolia* bark extract and hyaluronic acid, and also the use of active ingredient combinations of *magnolia* bark extract and hyaluronic acid for tightening and/or firming the skin, in particular in cosmetic or dermatological preparations, overcomes the disadvantages of the prior art.

The use of active ingredient combinations according to the invention and/or cosmetic or dermatological preparations with an effective content of such active ingredient combinations e.g. in the form of the examples listed below—leads in a surprising manner to a considerable improvement in the appearance of the skin.

As a result of using preparations according to the invention, the skin moisture is also increased and the lipid synthesis is stimulated and therefore the skin volume is influenced in a positive manner.

BRIEF DESCRIPTION OF THE DRAWING

In the accompanying drawing,

FIG. 1 illustrates the results regarding induction of adipogenesis obtained in the experiments set forth immediately below.

DETAILED DESCRIPTION OF THE INVENTION

It was surprising that by applying active ingredient combinations according to the invention and/or cosmetic or dermatological preparations with an effective content of such active ingredient combinations, the wrinkle depth and wrinkle number of intrinsically or extrinsically aged skin is reduced and consequently the appearance of aging skin is improved.

It was also surprising that by applying active ingredient combinations according to the invention and/or cosmetic or dermatological preparations with an effective content of such active ingredient combinations, the elasticity of the skin, and therefore cellulite and/or the appearance of so-called "orange peel skin", is improved.

*Magnolia* is a plant genus in the family of Magnoliaceae. This contains about 230 species which originate from Eastern Asia and America. According to the invention, the *magnolia* bark extract can in principle be taken from all species of the genus *magnolia*, although preference is given to *Magnolia grandiflora*, and in particular *Magnolia officinalis*.

*Magnolia* bark is used in traditional Chinese medicine (TCM) particularly for "stagnation of qi" (low energy), emotional stress, inflammations, internal agitation and anxiety states.

The extract used is prepared with the help of supercritical $CO_2$ or ethanol or an ethanol/water mixture.

Magnolol is characterized by the following structure:

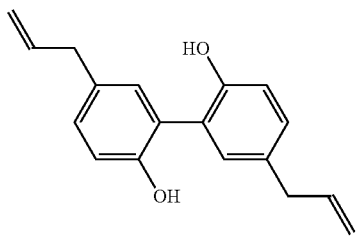 [SMILES: C=CCc1ccc(O)c(-c2cc(CC=C)ccc2O)c1]

Honokiol is characterized by the following structure:

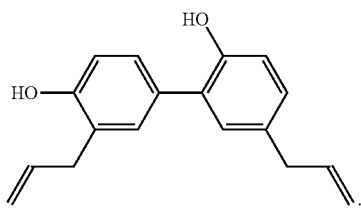 [SMILES: C=CCc1ccc(O)c(-c2ccc(O)c(CC=C)c2)c1]

The cosmetic or dermatological preparations according to the invention can have the customary composition and serve for the treatment, care and cleaning of the skin and/or the hair and as a make-up product in decorative cosmetics. They comprise preferably 0.001% by weight to 10% by weight, preferably 0.05% by weight to 5% by weight, in particular 0.1-2.0% by weight, based on the total weight of the preparations, of *magnolia* bark extract.

Hyaluronic acid is a polysaccharide derivative which is characterized by the following structural element:

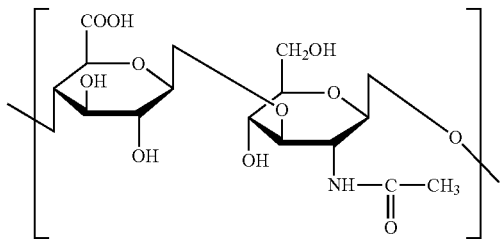

Hyaluronic acid is a glycosaminoglycan which occurs in connective tissue, in vitreous bodies, in the umbilical cord and in the synovial fluid of joints. Hyaluronic acid is present to a particularly high degree in early embryonal stages and coacts here on cell migrations by, as a result of its looser structure and a high water content, shielding cells expressing on its surface from each other and thus permitting their free mobility. Hyaluronic acid is involved in wound healing.

Hyaluronic acid is a high molecular weight compound with molecular weights between 40 000 and several million. It is advantageous in the context of the present invention if the hyaluronic acid used has an average molar mass maximum between 40 kDa and 60 kDa and/or 1000 kDa and 2200 kDa. It is equally advantageous according to the invention if the hyaluronic acid is present in protonated form, as salt, as partly protonated salt, dissociated or partly dissociated in solution.

According to the invention, the concentration of hyaluronic acid, based on the total weight of the preparation, is advantageously 0.001 to 10% by weight, preferably from 0.05 to 5% by weight and very particularly preferably from 0.01 to 2% by weight, in each case based on the total weight of the preparation.

Advantageously, weight ratios of *magnolia* bark extract and hyaluronic acid from the ranges 10:1 to 1:1, preferably from 8:1 to 2:1, particularly preferably from 6:1 to 3:1, are selected.

According to the invention, customary antioxidants can be added to preparations which comprise the active ingredient combinations according to the invention.

The antioxidants are advantageously selected from the group consisting of amino acids (e.g. glycine, histidine, tyrosine, tryptophan) and derivatives thereof, imidazoles (e.g. urocanic acid) and derivatives thereof, peptide such as D,L-carnosine, D-carnosine, L-carnosine and derivatives thereof (e.g. anserine), carotenoids, carotenes) e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and also salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, alaninediacetic acid, flavonoids, polyphenols, catechins, vitamin C and derivatives (e.g. ascorbyl palmitate, Mg ascorbyl phosphate, ascorbyl acetate), tocopherols and derivatives (e.g. vitamin E acetate), and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives suitable according to the invention (salts, esters, ethers, sugars, nucleotides, nucleosides, peptides and lipids) of these specified active ingredients.

The amount of the antioxidants (one or more compounds) in the preparations is preferably 0.001 to 30% by weight, particularly preferably 0.05-20% by weight, in particular 1-10% by weight, based on the total weight of the preparation.

Particularly advantageous embodiments of the present invention consist in active ingredient combinations of *magnolia* bark extract, hyaluronic acid and an anise fruit extract, and also the use of active ingredient combinations of *magnolia* bark extract, hyaluronic acid and an anise fruit extract for the tightening and/or firming of the skin, in particular in cosmetic or dermatological preparations.

Particularly advantageous according to the invention is an aqueous fruit extract of anise (INCI: *Pimpinella anisum* fruit extract), which is rich in inorganic minerals such as sodium and magnesium ions, particularly in potassium ions, and is preserved with butylene glycol 0.36% and parabens 0.14% and is obtainable by enzymatic hydrolysis of anise fruits solubilized in water, where the ratio of raw material to extract is about 1:2 and is available under the tradename Bioxylift® from SILAB, (Brive Cedex, France).

Anise fruit extract (Bioxylift®, SILAB) is an aqueous fruit extract from anise.

The extract has an amber-like color and has a characteristic anise odor. It is rich in inorganic minerals such as sodium and magnesium ions, but particularly in potassium ions.

The specific composition is:
Dry mass: 40-60 g/l
Mineral ash: 11-18 g/l
Total protein: 12-20 g/l
pH: 4.5-5.5

The extract can be produced and stored with or without preservation. Its production is described in the International patent application WO 02/102347.

Preferably, cosmetic or dermatological preparations according to the invention comprise 0.001 to 30% by weight, preferably 0.1 to 15% by weight, particularly preferably 0.5 to 7% by weight of, in each case based on the total weight of the preparation.

According to the invention, particular preference is given to weight ratios of
a) *magnolia* bark extract
b) hyaluronic acid and
c) anise fruit extract
selected as a:b:c, where a, b and c, independently of one another, can be rational numbers from 1 to 50, preferably from 1 to 40.

For hyaluronic acid with an average molar mass maximum between 1000 kDa and 2200 kDa, particular preference is given to a weight ratio of about 5:1:30 to 3:1:26. For hyaluronic acid with an average molar mass maximum between 40 kDa and 60 kDa, a weight ratio of about 8:1:45 to 3:1:26 is preferred.

The prophylaxis and/or the cosmetic or dermatological treatment with the active ingredient used according to the invention and/or with the cosmetic or topical dermatological preparations with an effective content of active ingredient used according to the invention takes place in the usual way, specifically in such a way that the active ingredient used according to the invention and/or the cosmetic or topical dermatological preparations with an effective content of active ingredient used according to the invention is applied to the areas of skin in question.

Emulsions according to the invention in the context of the present invention, e.g. in the form of a cream, a lotion, a cosmetic milk are advantageous and comprise e.g. fats, oils, waxes and/or other fatty bodies, and also water and one or more emulsifiers as are customarily used for such a type of formulation.

It is also possible and advantageous in the context of the present invention to add the active ingredient used according to the invention to aqueous systems and/or surfactant preparations for cleaning the skin and the hair.

It is naturally known to the person skilled in the art that exacting cosmetic compositions are in most cases inconceivable without the customary auxiliaries and additives. These include, for example, consistency regulators, fillers, perfume, dyes, emulsifiers, additional active ingredients such as vitamins or proteins, light protection agents, stabilizers, insect repellents, alcohol, water, salts, antimicrobially, proteolytically or keratolytically effective substances etc.

Corresponding requirements on the formulation of medical preparations apply mutatis mutandis.

Medicinal topical compositions in the context of the present invention generally comprise one or more medicaments in an effective concentration. For the sake of simplicity, in order to make a clear distinction between cosmetic and medicinal use and corresponding products, reference is made to the legal provisions of the Federal Republic of Germany (e.g. Cosmetics Ordinance, Foods and Drugs Act).

In this connection, it is likewise advantageous to add the active ingredient used according to the invention as additive to preparations which already comprise other active ingredients for other purposes.

The cosmetic and/or dermatological formulations according to the invention can have the customary composition and serve to treat the skin and/or the hair in the sense of a dermatological treatment or a treatment in the sense of care cosmetics. However, they can also be used in make-up products in decorative cosmetics or in cosmetic and dermatological cleaning products.

If the cosmetic or dermatological preparation is a solution or lotion, solvents which can be used are: water or aqueous solutions, also oils, such as triglycerides of capric acid or caprylic acid, but preferably castor oil, fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids, but also alcohols, diols or polyols of low carbon number, and also ethers thereof, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

In particular, mixtures of the aforementioned solvents are used, thus as in the case of alcoholic solvents water can be an advantageous further constituent.

Cosmetic and dermatological preparations according to the invention, also e.g. for protecting the skin against UV rays, can be present in various forms, as are used e.g. customarily for this type of preparations. Thus, they can be e.g. a solution, an emulsion of the water-in-oil (W/O) type or of the oil-in-water (O/W) type, or a multiple emulsions, for example of the water-in-oil-in-water (W/O/W) type, oil-in-water-in-oil (O/W/O) type, a gel, a hydrodispersion, a lamellar phase, a liquid isotropic solution phase, a micellar phase, a solid or dispersed mono- or polyhexagonal phase, a solid or dispersed mono- or polycubic phase, a lyotropic phase, a crystalline phase, a solid stick or else an aerosol.

The active ingredients according to the invention can also be used particularly advantageously in microemulsions, for example as described in the German laid-open specification DE-195 9 079.

The oil phase of the preparations according to the invention is advantageously selected from the group of the esters of saturated and/or unsaturated, branched and/or unbranched alkane carboxylic acids of a chain length from 3 to 30 C atoms and saturated and/or unsaturated, branched and/or unbranched alcohols of a chain length from 3 to 30 C atoms, from the group of esters of aromatic carboxylic acids and saturated and/or unsaturated, branched and/or unbranched alcohols of a chain length from 3 to 30 C atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semi-synthetic and natural mixtures of such esters, e.g. jojoba oil.

Furthermore, the oil phase can advantageously be selected from the group of branched and unbranched hydrocarbons and hydrocarbon waxes, silicone oils, dialkyl ethers, the group of saturated or unsaturated, branched or unbranched alcohols, and also fatty acid triglycerides, namely the triglycerol esters of saturated and/or unsaturated, branched and/or unbranched alkane carboxylic acids of a chain length from 8 to 24, in particular 12-18 C atoms. The fatty acid triglycerides can for example be advantageously selected from the group of synthetic, semi-synthetic and natural oils, e.g. olive oil, sunflower oil, soybean oil, peanut oil, rapeseed oil, almond oil, palm oil, coconut oil, palm kernel oil and the like.

Any desired mixtures of such oil and wax components can also be used advantageously in the context of the present invention.

The oil phase is advantageously selected from the group 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether.

Mixtures of $C_{12-15}$-alkyl benzoate and 2-ethyhexyl isostearate, mixtures of $C_{12-15}$-alkyl benzoate and isotridecyl isononanoate, and also mixtures of $C_{12-15}$-alkyl benzoate, 2-ethylhexyl isostearate and isotridecyl isononanoate are particularly advantageous.

Of the hydrocarbons, paraffin oil, squalane and squalene are to be used advantageously in the context of the present invention.

The oil phase can advantageously also have a content of cyclic or linear silicone oils or consist completely of such oils, although it is preferred to use an additional content of other oil phase components apart from the silicone oil or the silicone oils.

Advantageously, cyclomethicone (octamethylcyclotetrasiloxane) is used as silicone oil to be used according to the invention. However, other silicone oils are also to be used advantageously in the context of the present invention, for example hexamethylcyclotrisiloxane, polydimethylsiloxane, poly(methylphenylsiloxane).

Mixtures of cyclomethicone and isotridecyl isononanoate, and of cyclomethicone and 2-ethylhexyl isostearate are also particularly advantageous.

The content of the oil phase is advantageously between 1 and 50% by weight, based on the total weight of the preparations, preferably 2.5-30% by weight, particularly preferably 5-15% by weight.

For use, the cosmetic and/or dermatological formulations according to the invention are applied to the skin in an adequate amount in the manner customary for cosmetics and dermatologics.

Demonstration of Action:
Induction of Adipogenesis

Subcutaneous human preadipocytes isolated from the thigh region of various donors (LOT L041806, L080608) were commercially acquired from Zen-Bio Inc. (Research Triangle Park, N.C.).

Cultivation of the cells was carried out in basal medium (10% fetal calf serum (FCS), 2 mM L-glutamine, 100 U/ml penicillin and 100 µg/ml streptomycin; Cambrex, Verviers, Belgium) for 7 days at 37° C. and 5% $CO_2$ in a cell incubator. The cell culture medium was renewed on the first day and on the fourth day after sowing.

Subsequently, the cells were passaged into 96-well plates ($1\times10^4$ cells per well). 24 hours after passage into the 96-well plates, the cells were incubated with differentiation medium without indomethacin (basal medium with 10% fetal calf serum (FCS), 2 mM L-glutamine, 100 U/ml penicillin and 100 µg/ml streptomycin, 10 µg/ml insulin, 1 µM dexamethasone and 500 µM isobutylmethylxanthine; Cambrex, Verviers, Belgium) with the following active ingredients and active ingredient combinations: *magnolia* bark extract (10 µM), hyaluronic acid (LMW, 1%), *magnolia* bark extract (10 µM)+hyaluronic acid (LMW, 1%).

The "negative control" used was a cell population which was cultivated without the addition of active ingredient. The "positive control" used was rosiglitazone (2.25 µM). The coloration of the triglyceride accumulation during the differentiation was carried out on the 7th day after induction by means of AdipoRed reagent (Cambrex, Verviers, Belgium) in accordance with the manufacturers instructions. Finally, the fluorescence (ex 485 nm, em 572 nm) was determined using an Infinite M200 plate reader (Tecan, Crailsheim, Germany).

The examples below serve to illustrate the embodiments of the present inventions.

| INCI | Example 1 | Example 2 | Example 3 | Example 4 | Example 5 |
|---|---|---|---|---|---|
| 1,2-Hexanediol | 0.50 | | 0.50 | 0.70 | 0.60 |
| Acrylate/C10-30 alkyl acrylate crosspolymer | 0.10 | 0.20 | | 0.15 | 0.10 |
| Bis-ethylhexyloxyphenol methoxyphenyltriazine | 1.00 | 1.50 | 2.00 | 0.50 | |
| Butylene glycol dicaprylate/dicaprate | | | 2.50 | 1.00 | |
| Butylmethoxydibenzoylmethane | 4.00 | 2.00 | | 3.00 | |
| *Butyrospermum Parkii* (Shea Butter) | 6.00 | 7.00 | 1.00 | 3.00 | |
| C12-15 alkyl benzoate | 2.00 | 1.00 | | 1.00 | |
| Caprylic/capric triglyceride | | | | 3.00 | 4.00 |
| Carbomer | 0.30 | 0.10 | 0.40 | 0.20 | 0.10 |
| Cetearyl alcohol | 1.00 | 2.50 | 2.00 | 3.00 | |
| Cetyl alcohol | 1.00 | 1.00 | | | 1.50 |

-continued

| INCI | Example 1 | Example 2 | Example 3 | Example 4 | Example 5 |
|---|---|---|---|---|---|
| Cetyl palmitate | | | 2.50 | 2.00 | 4.00 |
| Dibutyl adipate | 3.00 | 3.00 | | | |
| Diethylamino hydroxybenzoyl hexyl benzoate | | | 3.50 | | |
| Dimethicone | | 0.50 | 0.80 | | 0.30 |
| Ethylhexyl glycerol | | | 0.25 | 0.30 | 0.50 |
| Ethylhexyl salicylate | 4.50 | 5.00 | | 3.00 | |
| Ethylhexyl triazine | | | 2.50 | | |
| Glycerol | 10.00 | 9.00 | 8.00 | 12.00 | 8.00 |
| Glycerol stearate | 2.50 | 2.00 | | 2.80 | |
| Glycerol stearate citrate | | | 1.50 | | 2.50 |
| Hydrogenated coco glycerides | 1.00 | 2.00 | 2.00 | 1.00 | 3.50 |
| Isopropyl palmitate | | | | | 2.50 |
| *Magnolia Officinalis* Bark Extract | 0.50 | 0.50 | 0.40 | 0.80 | 0.70 |
| Methyl paraben | | 0.20 | | | |
| Methylpropanediol | 2.00 | 1.50 | | 2.00 | 1.00 |
| Sodium hyaluronate, average molar mass maximum between 1000 kDa and 2200 kDa | 0.15 | | 0.10 | | 0.20 |
| Sodium hyaluronate, average molar mass maximum between 40 kDa and 60 kDa | | 0.10 | | 0.15 | |
| Octyldodecanol | | | 2.00 | 2.00 | 3.00 |
| Panthenol | | 2.00 | | | 5.00 |
| Perfume | q.s. | q.s. | q.s. | q.s. | q.s. |
| Phenoxyethanol | 0.60 | 0.60 | 0.80 | 0.40 | 0.80 |
| Phenylbenzimidazolsulfonic acid | 2.00 | 1.00 | | 0.50 | |
| Polymethylsilsesquioxane | | | 2.00 | 1.00 | 1.00 |
| Sodium stearoyl glutamate + sodium chloride | 0.20 | 0.50 | | 0.10 | |
| Stearyl alcohol | | | 1.00 | | 2.00 |
| Synthetic beeswax | 1.00 | | 2.00 | 2.00 | 3.00 |
| Water | ad 100% | ad 100% | ad 100% | ad 100% | ad 100% |
| Water + *Pimpinella Anisum* (anise fruit extract) | 4.00 | 3.50 | 2.80 | 5.00 | 5.50 |
| Water + sodium hydroxide | 1.10 | 0.90 | 0.40 | 0.70 | 0.10 |
| Water + trisodium EDTA | 1.20 | 1.00 | 1.10 | 0.80 | 1.00 |

What is claimed is:

1. A topical cosmetic or dermatological preparation, wherein the preparation comprises hyaluronic acid and from 0.001% to 10% by weight, based on a total weight of the preparation, of *magnolia* bark extract, the hyaluronic acid comprising hyaluronic acid having an average molar mass maximum of from 40 kDa to 60 kDa and/or hyaluronic acid having an average molar mass maximum of from 1,000 kDa to 2,200 kDa, and a weight ratio of *magnolia* bark extract and hyaluronic acid being from 10:1 to 1:1.

2. The preparation of claim 1, wherein the preparation further comprises anise fruit extract, a weight ratio *magnolia* bark extract : hyaluronic acid : anise fruit extract being from about 5:1:30 to about 3:1:26 if the hyaluronic acid has an average molar mass maximum of from 1,000 kDa to 2,200 kDa, and from about 8:1:45 to 3:1:26 if the hyaluronic acid has an average molar mass maximum of from 40 kDa to 60 kDa.

3. The preparation of claim 2, wherein the anise fruit extract is obtained by enzymatic hydrolysis of anise fruits solubilized in water.

4. The preparation of claim 1, wherein the preparation is an emulsion.

5. The preparation of claim 1, wherein the preparation comprises from 0.05% to 10% by weight, based on a total weight of the preparation, of hyaluronic acid.

6. The preparation of claim 5, wherein the hyaluronic acid comprises hyaluronic acid having an average molar mass maximum of from 40 kDa to 60 kDa.

7. The preparation of claim 5, wherein the hyaluronic acid comprises hyaluronic acid having an average molar mass maximum of from 1,000 kDa to 2,200 kDa.

8. The preparation of claim 2, wherein the preparation comprises from 0.05% to 10% by weight, based on a total weight of the preparation, of hyaluronic acid.

9. The preparation of claim 8, wherein the hyaluronic acid comprises hyaluronic acid having an average molar mass maximum of from 40 kDa to 60 kDa.

10. The preparation of claim 8, wherein the hyaluronic acid comprises hyaluronic acid having an average molar mass maximum of from 1,000 kDa to 2,200 kDa.

11. The preparation of claim 8, wherein the preparation comprises from 0.1% to 15% by weight, based on a total weight of the preparation, of anise fruit extract.

12. The preparation of claim 1, wherein the preparation comprises from 0.05% to 5% by weight of *magnolia* bark extract.

13. The preparation of claim 12, wherein the preparation comprises from 0.05% to 5% by weight, based on a total weight of the preparation, of hyaluronic acid.

14. The preparation of claim 2, wherein the preparation comprises from 0.001% to 30% by weight, based on a total weight of the preparation, of anise fruit extract.

15. The preparation of claim 1, wherein the preparation further comprises one or more organic light protection agents.

16. The preparation of claim 15, wherein the one or more organic light protection agents comprise one or more of bis-hexyloxyphenol methoxyphenyltriazine, butylmethoxydibenzoylmethane, diethylamino hydroxybenzoyl hexyl benzoate, ethylhexyl salicylate, ethylhexyl triazine and phenylbenzimidazolesulfonic acid.

17. The preparation of claim 1, wherein the preparation is present as a cream, a lotion or a cosmetic milk.

18. A topical cosmetic or dermatological preparation, wherein the preparation comprises, based on a total weight of the preparation, from 0.05% to 5% by weight of *magnolia* bark extract, from 0.05% to 5% by weight of hyaluronic acid, and from 0.1% to 15% by weight of anise fruit extract.

19. The preparation of claim 18, wherein the hyaluronic acid comprises hyaluronic acid having an average molar mass maximum of from 40 kDa to 60 kDa and/or hyaluronic acid having an average molar mass maximum of from 1,000 kDa to 2,200 kDa.

20. The preparation of claim 18, wherein the preparation further comprises one or more organic light protection agents.

\* \* \* \* \*